United States Patent [19]
Takeuchi et al.

[11] Patent Number: 4,950,900
[45] Date of Patent: Aug. 21, 1990

[54] HEATED INFRARED GAS ANALYZER USING A PYROELECTRIC INFRARED SENSOR

[75] Inventors: Kousuke Takeuchi; Kenichi Shibata, both of Hirakata; Toshiharu Tanaka, Higashiosaka; Seiji Nishikawa, Ibaraki; Kazuhiko Kuroki, Uji; Shoichi Nakano, Hirakata, all of Japan

[73] Assignee: Sanyo Electric Co., Ltd., Moriguchi, Japan

[21] Appl. No.: 320,651

[22] Filed: Mar. 8, 1989

[30] Foreign Application Priority Data

Mar. 10, 1988 [JP] Japan .................. 63-57114

[51] Int. Cl.$^5$ .................. G01N 21/17; G01N 21/71; G01J 1/00
[52] U.S. Cl. .................. 250/346; 250/338.3; 250/343; 250/352
[58] Field of Search .................. 250/338.3, 346, 352, 250/353, 343

[56] References Cited

U.S. PATENT DOCUMENTS

| | | | |
|---|---|---|---|
| 4,157,470 | 6/1979 | Kotaka et al. | 250/345 |
| 4,194,118 | 3/1980 | Kotaka et al. | 250/352 X |
| 4,293,768 | 10/1981 | Adachi et al. | 250/338.3 |
| 4,307,388 | 12/1981 | Doenges et al. | 250/352 X |
| 4,501,968 | 2/1985 | Edi et al. | 250/352 X |
| 4,516,027 | 5/1985 | Schimmelpfennig et al. | 250/338.3 |

FOREIGN PATENT DOCUMENTS 5784447 11/1980 Japan .

OTHER PUBLICATIONS

"Modulation Typed Micro Noncontact Temperature Sensor", Kuwano et al., *Electronic Parts and Materials*, vol. 23, No. 8, pp. 96–100.

*Primary Examiner*—Constantine Hannaher
*Assistant Examiner*—J. Eisenberg
*Attorney, Agent, or Firm*—Armstrong, Nikaido, Marmelstein, Kubovcik & Murray

[57] ABSTRACT

An infrared gas analyzer using a pyroelectric infrared sensor, which includes a heating unit for heating the infrared sensor, a heating sensor for detecting its heating temperature and a temperature sensor for detecting the ambient temperature of the infrared sensor, and controls the heating unit so as to retain the ambient temperature of the infrared sensor at a constant so that the output error is small irrespective of the change in ambient temperature.

5 Claims, 5 Drawing Sheets

HEATED INFRARED GAS ANALYZER USING A PYROELECTRIC INFRARED SENSOR

BACKGROUND OF THE INVENTION

1. Field of the Invention

The present invention relates to an infrared gas analyzer comprising a pyroelectric infrared sensor, particularly, it relates to an infrared gas analyzer with improved temperature characteristics of the infrared sensor.

2. Description of the Prior Art

An infrared gas analyzer of this type has been disclosed in, for example, "Infrared Gas Analyzer (ULTRAMAT-S)" in Fuji Technical Review Vol. 50, No. 7, Page 368 published in 1977. For an infrared sensor of this type of infrared gas analyzer, conventionally, a microflow type sensor utilizing gaseous heat expansion or a thermistor type sensor utilizing temperature characteristics of the electric resistance has been used.

In the infrared gas analyzer using such an infrared sensor, the change of the ambient temperature does not affect the detecting output of gas, since the same pressure variation occurs in a sample detecting bath and a standard detecting bath for a microflow type sensor. While, in the case of the thermistor type sensor, as the output changes due to temperature variations, the board temperature is retained at a predetermined temperature by an indirectly-heated heater disposed near the board to compensate the temperature characteristics required for the infrared sensor.

In addition to the infrared sensors aforementioned, a pyroelectric infrared sensor may be used. The pyroelectric infrared sensor is designed to detect an infrared ray by irradiating the infrared ray onto a pyroelectric material so as to produce an electric charge by a pyroelectric effect, and thereby measuring the electric voltage produced in the pyroelectric material. In the pyroelectric infrared sensor, if the pyroelectric material temperature itself changes, the electric voltage is produced by a pyroelectric effect even when the infrared ray is not irradiated, so that when using it as the infrared detector, the pyroelectric material temperature and the ambient temperature are preferably kept at a constant as much as possible.

When the pyroelectric infrared sensor is used in the infrared sensor, since it has a higher sensitivity than the microflow type sensor and the thermistor type sensor, a gas analyzer having a higher resolution may be realized, and still the temperature characteristics has to be compensated. Since the pyroelectric infrared sensor is a so-called differential detector in which output is produced by the temperature variations (to the time elapsed) of a pyroelectric element, when arranging the indirectly-heated heater in the vicinity of the pyroelectric element, there is the possibility that sudden temperature variations may cause the sensor to generate an erroneous output, therefore, the sudden change of temperature must be prevented by such a means as increasing the thermal capacity of the indirectly-heated heater.

However, if a material having a high specific heat is wound around the heater to increase the thermal capacity of the indirectly-heated heater, such an indirectly-heated heater becomes larger and can not be contained in the sensor case.

When the infrared ray chopper is a solid-state device and the ultra-small pyroelectric infrared sensor incorporated therein is used (refer to Japanese Patent Application Laid Open No. 82136/1983), it is difficult to install the indirectly-heated heater. Likewise, when the infrared sensor is heated by a heater from outside the sensor case, since heat takes time to reach the infrared detecting unit, a problem is encountered such that the electric heating power of the heater can not be controlled properly even if controlled by detecting the temperature in the sensor case.

SUMMARY OF THE INVENTION

The present invention has been devised in view of the aforesaid circumstances, and the infrared gas analyzer according to the present invention comprises an infrared sensor consisting of a pyroelectric infrared detecting unit contained in a sensor case, and is characterized by comprising a heating unit for heating the infrared sensor to a predetermined temperature, a heater temperature sensor for detecting the heating temperature of the infrared sensor by the heating unit, an inner temperature sensor for detecting the temperature in the sensor case, and a controlling device for controlling the electric heating power of the heating unit in accordance with the difference between the output of the heater temperature sensor and the difference obtained between the output of the inner temperature sensor at energizing this analyzer and the predetermined value thereof.

It is an object of the present invention to provide an infrared gas analyzer which can produce stable output irrespective of the change in ambient temperature by disposing a heating device and controlling it to retain the infrared sensor at a predetermined temperature stably.

It is another object of the present invention to provide an infrared gas analyzer which can be kept compact as compared with the prior art by disposing the heating device for heating the infrared sensor in a dead space therein.

The above and further objects and features of the invention will more fully be apparent from the following detailed description with accompanying drawings.

DESCRIPTION OF THE PREFERRED EMBODIMENTS

The present invention will be described in detail with reference to the drawings showing its embodiment as follows.

Figure 1:
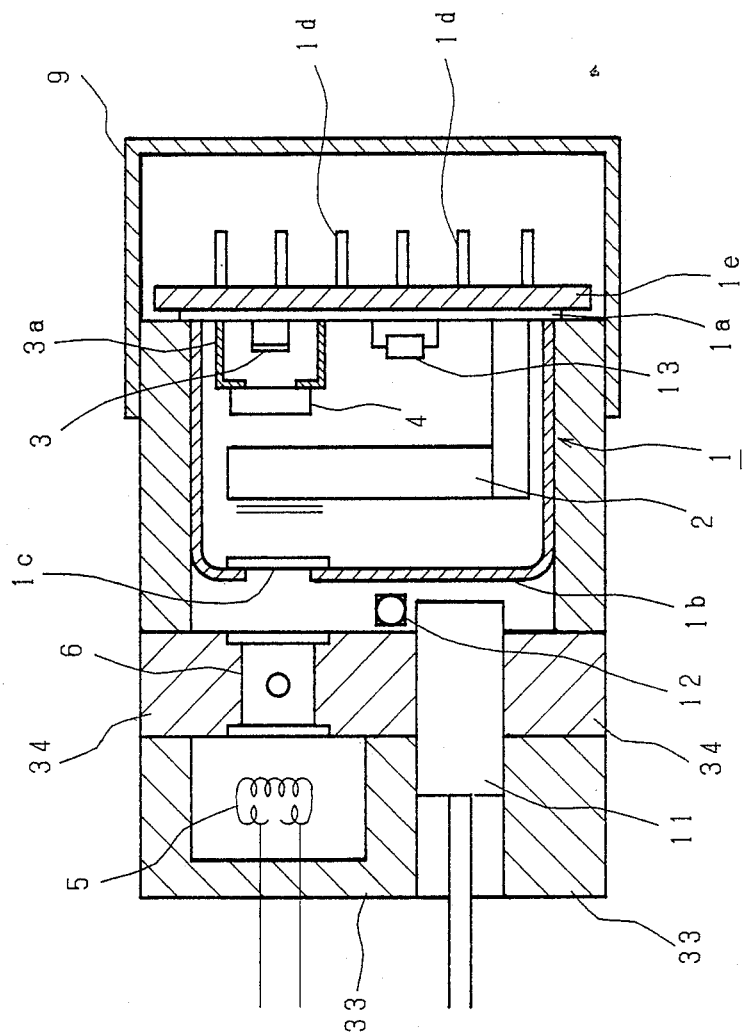
FIG. 1 is a sectional side view showing the internal structure of an infrared gas analyzer according to the present invention.
Figure 2:
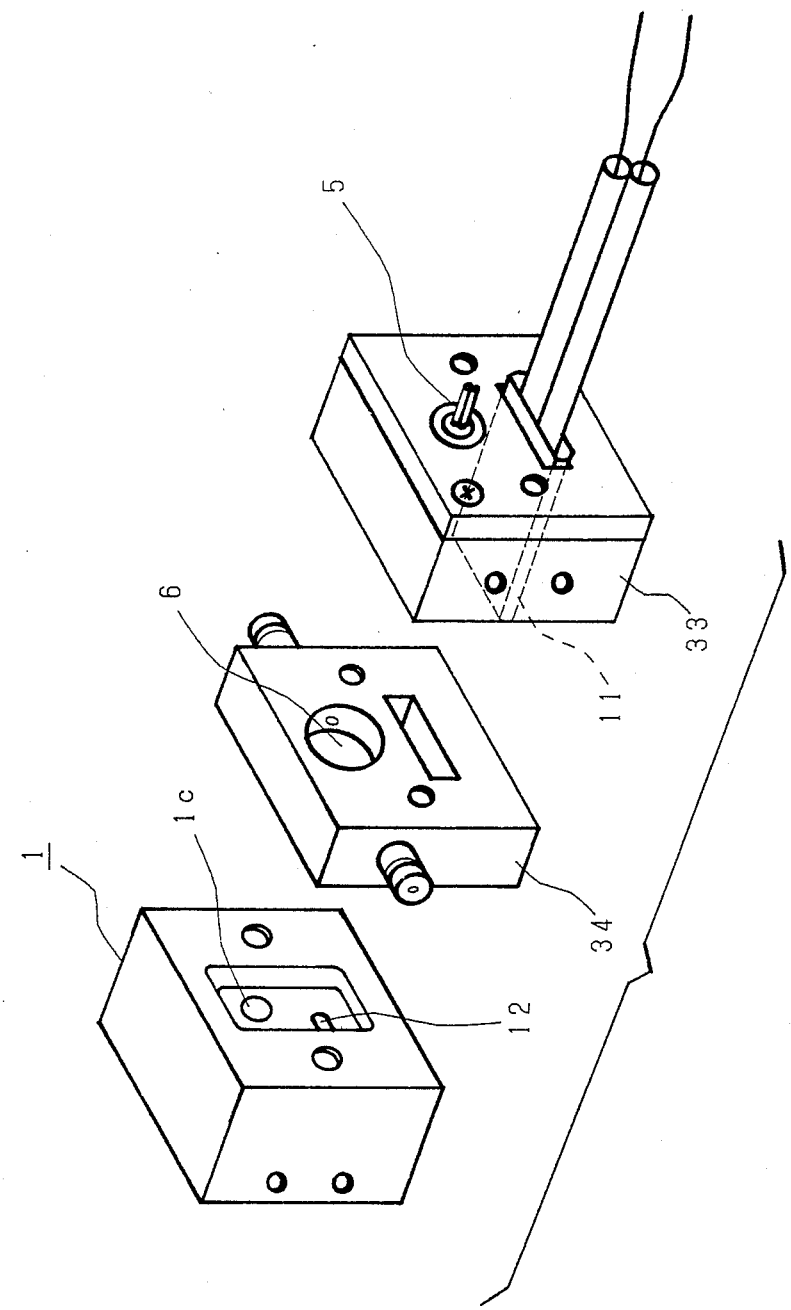
FIG. 2 is a perspective view showing an external view thereof.

FIG. 1 is an internal structural view of an infrared gas analyzer according to the present invention, and FIG. 2 is its external perspective view.

In the drawing, on the upper surface of a sensor case 1b of a pyroelectric infrared sensor 1 whose bottom opening is closed by a stem 1a, a window 1c closed by an infrared ray transmitting plate is provided, and an L-shaped infrared ray chopper 2 and an infrared detecting unit 3 opposing the window 1c via the infrared ray chopper 2 are incorporated in the sensor case 1b. The infrared detecting unit 3 is contained in a case 3a fixed on the stem 1a, and an opening of the case 3a between the infrared detecting unit 3 and the infrared ray chopper 2 is closed by an optical filter 4 disposed thereon which transmits only the absorption wave length of gas to be detected. On the stem 1a, an inner temperature sensor 13 which is a second temperature sensor for detecting the temperature in the vicinity of the infrared detecting unit 3 is installed. The infrared sensor 1, infrared detecting unit 3 and inner temperature sensor 13 are connected to terminals 1d, 1d. . . mounted on a printed circuit board 1e. A terminal cover 9 is provided over the portion where the terminals 1d, 1d. . . are disposed. On the side of window 1c of the sensor case 1b and opposing the window 1c, a holder 34 for holding a gas cell unit 6 for introducing gas to be detected is installed at a suitable interval from the window 1c, and on the opposite side of the gas cell unit 6 not opposing the window 1c, a containing unit 33 for containing an infrared light source 5 consisting of a nickrome wire heating element is disposed. On the side where the window 1c is provided on the sensor case 1b, a heating unit 11 consisting of a heater is disposed through the containing unit 33 of the infrared light source 5 and the holding unit 34 of the gas cell unit 6 at a suitable interval from the sensor case 1b. Near the heating unit 11, a heater temperature sensor 12 consisting of, for example, a diode is arranged in a spaced relationship with the sensor case 1b. Respective lead wires of the infrared light source 5, heating unit 11 and heater temperature sensor 12 are led outwardly. The heating unit 11 and heater temperature sensor 12 are disposed in the infrared gas analyzer, taking advantage of a dead space therein.

The infrared gas analyzer functions as follows to detect the gas concentration. That is, infrared rays produced by the infrared light source 5 are incident on the infrared sensor 1 through the gas cell unit 6 and window 1c. The incident infrared rays are periodically interrupted by the infrared ray chopper 2 and only the infrared ray of the gas absorption wave length of the optical filter 4 is passed through, and its energy is detected by the infrared detecting unit 3 to output a signal corresponding to the energy detected. Therefore, if gas to be detected exists in the gas cell unit 6, the infrared rays are absorbed by the gas and the infrared energy arriving at the infrared detecting unit 3 is reduced, thus the gas concentration can be measured by measuring the reduced quantity.

Figure 3:
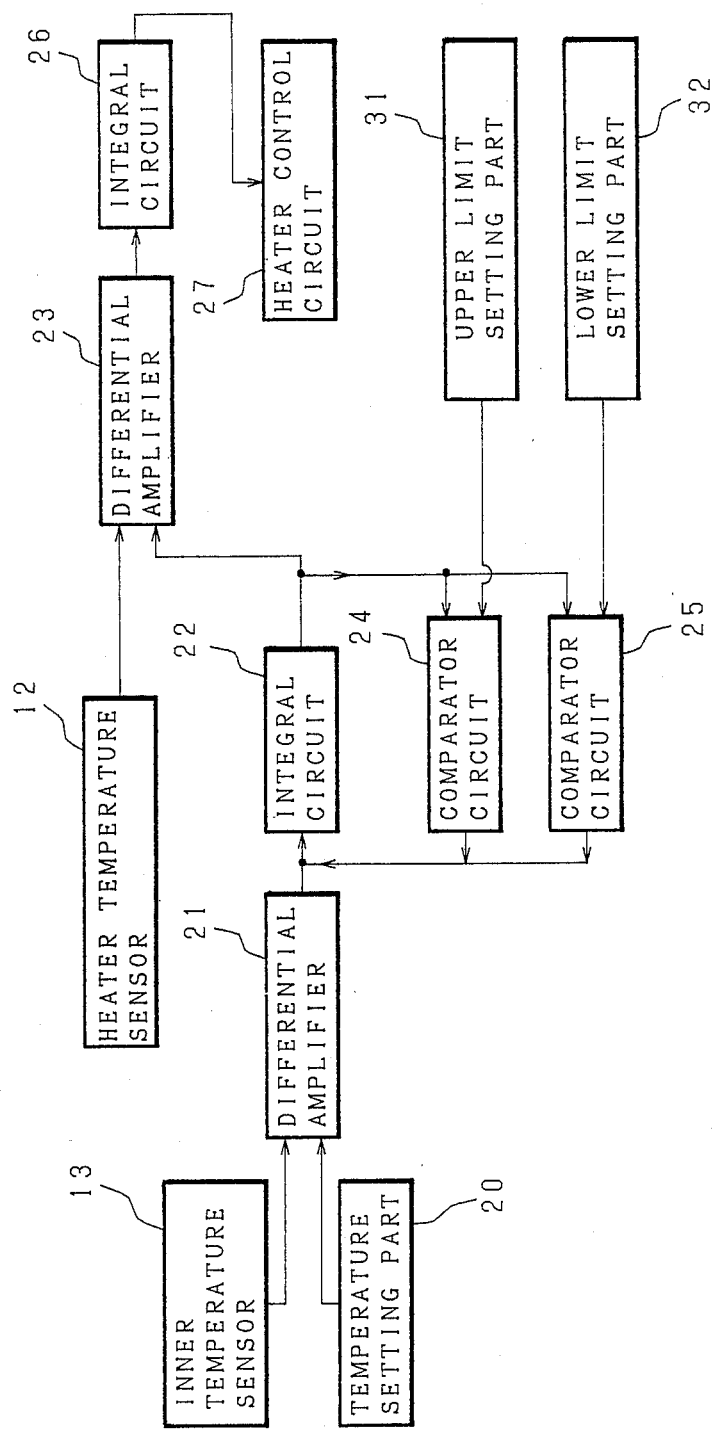
FIG. 3 is a block diagram of a temperature adjusting circuit.

FIG. 3 is a block diagram of a temperature adjusting circuit which is a temperature control means of the infrared gas analyzer. Output of an inner temperature sensor 13 and output of a temperature setting part 20 for setting its target value are given to a differential amplifier 21. Output of the differential amplifier 21 is given to an integral circuit 22, whose output is given to one end of a differential amplifier 23 and comparator circuits 24, 25. To the other end of the differential amplifier 23, the output of the heater temperature sensor 12 is given, and the output of the differential amplifier 23 is given to an integral circuit 26, whose output is given to a heater control circuit 27. To the comparator circuits 24, 25, an integral upper limit value corresponding to the minimum heater temperature from an integral upper limit setting part 31, and an integral lower limit value corresponding to the maximum heater temperature from an integral lower limit setting part 32 are given respectively. Output of the respective comparator circuits 24, 25 are given to the integral circuit 22.

Figure 4:
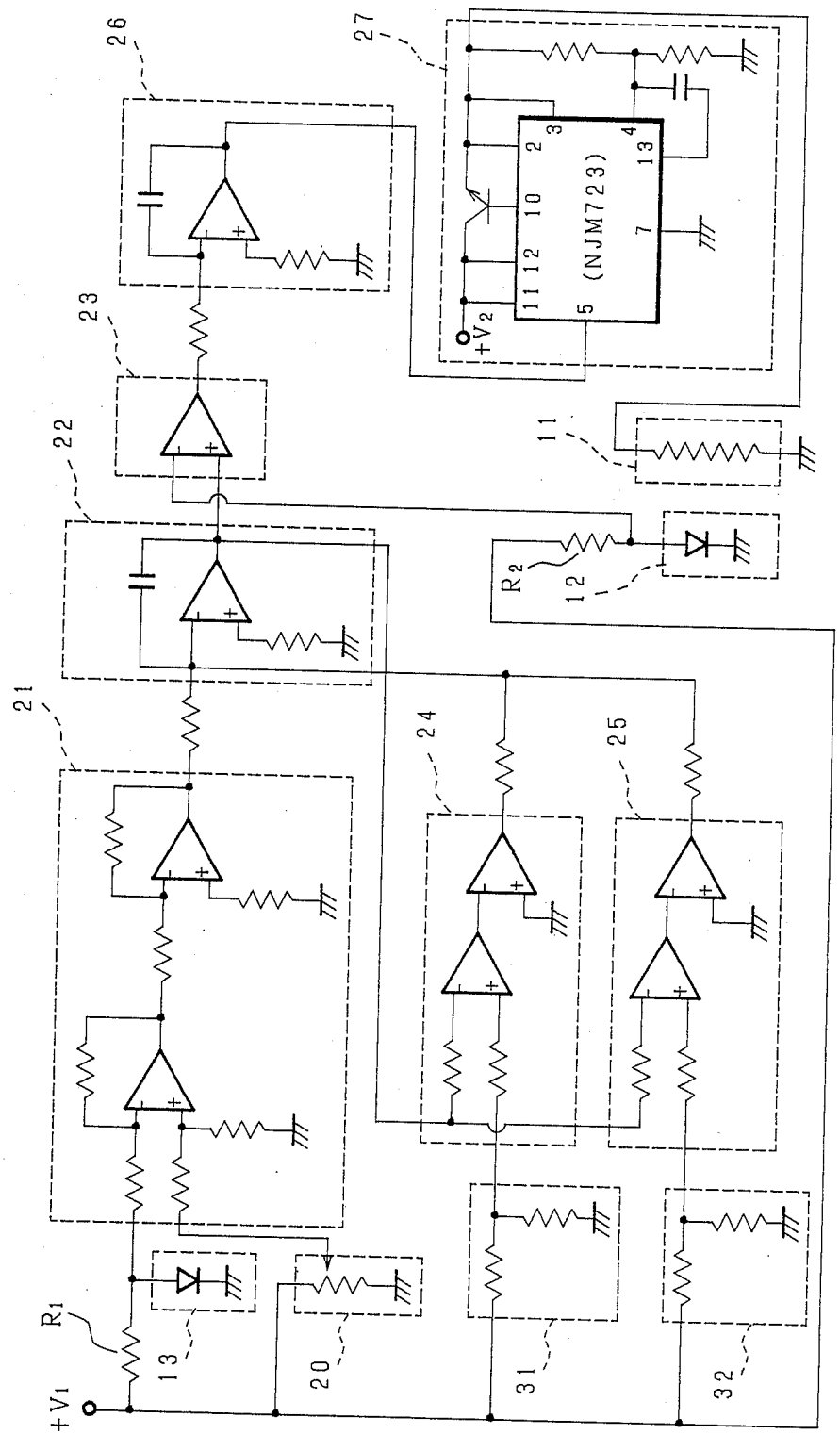
FIG. 4 is a specific circuit diagram of a temperature adjusting circuit.

FIG. 4 is a specific circuit diagram of a temperature adjusting circuit, in which the standard voltage $V_1$ is applied to the inner temperature sensor 13 consisting of a diode via a resistance $R_1$, and also given to the temperature setting part 20 consisting of a variable resistance, the integral upper limit setting part 31 and integral lower limit setting part 32 consisting of bleeder resistance, and further to one end of the heater temperature sensor 12 via a resistance $R_2$. Other ends of the temperature sensor 13, variable resistance 20, bleeder resistances 31, 32 and temperature sensor 12 are grounded. The output of the inner temperature sensor 13 is given to a negative input terminal of the differential amplifier 21 in which two operational amplifiers are connected in series for adapting the code of output signal of the amplifier 21 to the integral circuit 22, and the output of the temperature setting part 20 is given to its positive input terminal. The output signal from the differential amplifier 21 is given to the integral circuit 22 for integration. The integrated output is given to a positive input terminal of the differential amplifier 23 as well as to negative input terminals of the two comparator circuits 24, 25. The comparator circuit 24, 25 comprise two comparators respectively for adapting the code of output signal of them to the integral circuit 22, and the setting output of the integral upper limit (or lower limit) setting part 31 (or 32) is given to their positive input terminals. Compared outputs of the comparator circuits 24, 25 are fed back to the negative input terminal of the integral circuit 22.

To the negative input teminal of the differential amplifier 23, the detected output of the heater temperature sensor 12 is given. Output of the differential amplifier 23 is integrated in the integral circuit 26 and the integrated result is given to the heater control circuit 27. The heater control circuit 27 which is constituted by using, for example, a voltage regulator NJM723 manufactured by Shinnihon Musen Corp., is designed to control the voltages of the second and third terminals so as to equalize the voltages input to the fourth and fifth terminals. The controlled voltage is applied to the heating unit 11 to control the heating temparature thereof.

The temperature control operation of the heating unit 11 by a temperature adjusting circuit will be described as follows.

The differential amplifier 21 obtains the difference between output of the inner temperature sensor 13 and output of the temperature setting part 20 and gives the differential output to the integral circuit 22. The integral circuit 22 performs time integration of the output from the differential amplifier 21 and gives its output to the differential amplifier 23. The differential amplifier 23 obtains the difference of outputs between the heater temperature sensor 12 and the integral circuit 22 and gives the differential output to the integral circuit 26. The integral circuit 26 performs time integration of the output of the differential amplifier 23 and gives its output to the heater control circuit 27. The heater control circuit 27 controls the electric heating power of the heating unit 11 in response to the output of he integral circuit 26. While, the comparator circuit 24 compares the output of the integral circuit 22 with the integral upper limit value, and the comparator circuit 25 compares the output of the integral circuit 22 with the integral lower limit value, and they respectively give the positive and negative outputs to the integral circuit 22. The comparator circuits 24, 25 are provided to protect the infrared gas analyzer when noises are produced and at energizing the analyzer.

Now, the operation when diodes are used as the inner temperature sensor 13 and heater temperature sensor 12 will be described. The diode shows the characteristic of reducing forward voltage by the temperature rise. Therefore, when the output of the inner temperature sensor 13 is larger than that of the temperature setting part 20, namely, when the temperature of the inner temperature sensor 13 is lower than the setting of the temperature setting part 20, the differential amplifier 21 gives the output to the integral circuit 22 so as to reduce the output thereof.

When the output of the heater temperature sensor 12 is larger than that of the integral circuit 22, namely, when the temperature of the heater temperature sensor 12 is lower, the differential amplifier 23 gives the output to the integral circuit 26 so as to increase the output thereof, and the integral circuit 26 gives this output to the heater control circuit 27.

Though diodes are used in the inner temperature sensor 13 and heater temperature sensor 12, a thermistor may be used in lieu of the diode to allow the same operation as the diode by reducing both-end voltages thereof by the temperature.

Since the output of the inner temperature sensor 13 is larger than the temperature setting part 20 at energizing (the detected temperature of the inner temperature sensor is lower than the temperature setting value), the output of the integral circuit 22 is reduced from 0 V. Thereof, when the output of the integral circuit 22 is smaller than the integral lower limit value, the comparator circuits 24, 25 serve to increase the output of the integral circuit 22 to the integral lower limit value. Since the output of the heater temperature sensor 12 is larger than that of the integral circuit 22, the differential amplifier 23 increases the output of the integral circuit 26 and controls the heater control circuit 27 to supply the electric heating power to the heating unit 11.

When the heating unit 11 is energized to rise the ambient temperature of the infrared sensor 1, and the output of the inner temperature sensor 13 is reduced below the output of the temperature setting part 20, the output of the integral circuit 22 increases, thereby the output of the heater temperature sensor 12 becomes lower than the output of the integral circuit 22, and the output of the integral circuit 26 is reduced to lower the electric heating power and to increase the output of the heater temperature sensor 12 so as to correspond with the output of the integral circuit 22. By reducing the electric heating power, the ambient temperature of the infrared sensor 1 is lowered, and the output of the inner temperature sensor 13 approaches to the output corresponding to the setting voltage of the temperature setting part 20 to stabilize the ambient temperature of the infrared sensor 1.

Then, if the ambient temperature of the infrared gas analyzer changes, for example, if it falls, the heat quantity radiated from the outer surface of the infrared gas analyzer changes, and the ambient temperature of the infrared sensor 1 escapes from the stable state and falls. Thus, the output of the inner temperature sensor 13 increases and that of the integral circuit 22 is reduced. When the output of the heater temperature sensor 12 becomes larger than that of the integral circuit 22, the output of the integral circuit 26 increases to increase the electric heating power of the heating unit 11. Thereby, the infrared sensor 1 is heated to approach the output of the inner temperature sensor 13 to that of the temperature setting part 20. Then, the output of the integral circuit 22 becomes stable at the value differential from that before the inner temperature of the infrared gas analyzer changes.

By integrating the differential output between the inner temperature sensor 13 and the temperature setting part 20, and controlling the heating temperature of the heating unit 11 by utilizing the integrated value in such a manner, the ambient temperature of the infrared sensor 1 can be retained stably.

Figure 5:
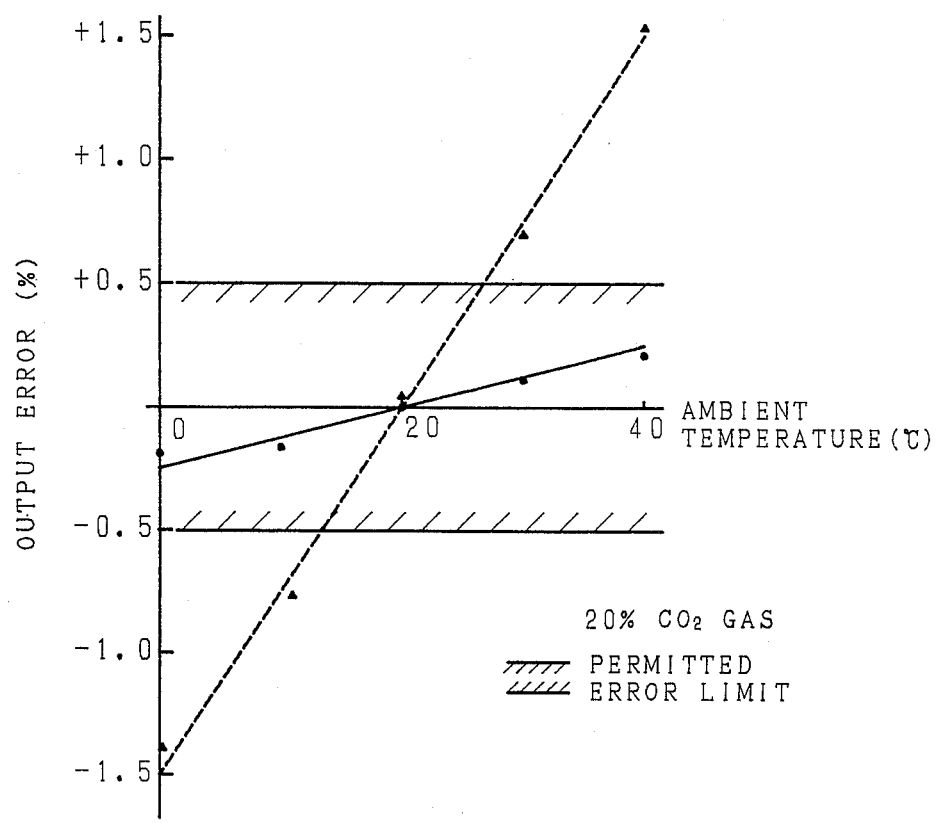
FIG. 5 is a graph showing the relationship between the ambient temperature and output error of an infrared gas analyzer.

Error characteristics of the infrared gas analyzer according to the present invention is shown in FIG. 5. In the figure, the output error (%) is plotted along the ordinate and the ambient temperature (° C) of the infrared gas analyzer is plotted along the abscissa, and the output error, when gas of 20% $Co_2$ is introduced into the gas cell unit 6, is shown. In the ambient temperature range of 0° to 40° required for the infrared gas analyzer, the output error characteristics of the present invention is within ±0.5% as shown by the full lines. While, the output error characteristics of the conventional infrared gas analyzer measured similarly, exceeds the permitted error limit (oblique-line area) of the output error at temperatures approximately below 15° C. or above 25° C. as shown by the broken lines. This is because, in the infrared gas analyzer of the present invention, the temperature change of infrared detecting unit 3 does not occur even when its ambient temperature changes, thereby assuring the advantage of the temperature control by the present invention.

As particularly described hereinabove, in the present invention, the heating temperature of the heating unit is detected by the heater temperature sensor, and the temperature in the sensor case of the infrared sensor by the inner temperature sensor to obtain the difference between the inner temperature sensor output and the predetermined value, and the difference of which between the heater temperature sensor output is obtained to control the electric heating power of the heating unit and to keep the temperature in the sensor case constant. Therefore, the gas concentration output error is kept within the permitted error limit even when the ambient temperature has changed extensively, and the size is same or smaller as compared with the conventional infrared gas analyzer, thus a superb infrared gas analyzer can be realized.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within the meets and bounds of the claims, or equivalence of such meets and bounds thereof are therefore intended to be embraced by the claims.

What is claimed is:

1. An infrared gas analyzer comprising:
   an infrared sensor having a pyroelectric infrared detecting unit;
   heating means for heating said infrared sensor to a predetermined temperature;
   a first temperature sensor for detecting a heating temperature by said heating means;

a second temperature sensor for detecting a temperature in a vicinity of said pyroelectric infrared detecting unit;

temperature setting means for setting a target value of temperature to be detected by said second temperature sensor;

means for obtaining a first difference between the temperature detected by said second temperature sensor and said target value; and heating control means for controlling said heating means in order to bring the temperature in the vicinity of said pyroelectric infrared detecting unit to said target value in response to a second difference between said first difference and a temperature detected by said first temperature sensor.

2. An infrared gas analyzer as set forth in claim 1, wherein said infrared detecting unit is contained in a protecting case.

3. An infrared gas analyzer as set forth in claim 1, further comprising first limit setting means for setting a maximum temperature of said heating means.

4. An infrared gas analyzer as set forth in claim 3, further comprising second limit setting means for setting a minimum temperature of said heating means.

5. An infrared gas analyzer comprising:

a containing unit for containing an infrared light source therein;

a holder for holding a gas cell unit which faces said light source and passes gas to be analyzed, wherein said infrared ray is irradiated to said gas from said light source;

an infrared sensor provided with a case, said case provided therein with (a) a chopping means for periodically interrupting infrared rays transmitting through said gas cell unit, (b) a pyroelectric infrared detecting unit for detecting the periodically interrupted infrared rays, and (c) a temperature sensor for detecting a temperature in a vicinity of said pyroelectric infrared detecting unit; and temperature adjusting means for adjusting a temperature of said pyroelectric infrared detecting unit, wherein said temperature adjusting means comprises (a) a heating means disposed through said containing unit and holder for heating said infrared sensor, (b) a heating temperature sensor provided near said heating means for detecting a heating temperature of said heating means and (c) heating control means for controlling said heating means.

* * * * *